United States Patent [19]

Brandon

[11] Patent Number: 5,807,933

[45] Date of Patent: Sep. 15, 1998

[54] CARBOXYL-CONTAINING PHENOLIC RESIN DEVELOPER AND METHOD OF PREPARATION

[75] Inventor: Richard L. Brandon, Chillicothe, Ohio

[73] Assignee: The Mead Corporation, Dayton, Ohio

[21] Appl. No.: 901,722

[22] Filed: Jun. 22, 1992

[51] Int. Cl.$^6$ .................................................. B41M 5/136
[52] U.S. Cl. .......................... 525/506; 525/507; 525/508; 525/534
[58] Field of Search ................................. 525/506, 507, 525/508, 534

[56] References Cited

U.S. PATENT DOCUMENTS

| | | |
|---|---|---|
| 3,224,550 | 12/1965 | Farnham et al. . |
| 3,224,559 | 12/1965 | Farnham et al. . |
| 3,672,935 | 6/1972 | Miller et al. . |
| 3,874,895 | 4/1975 | Hayashi et al. .......................... 428/199 |
| 3,934,070 | 1/1976 | Kimura et al. . |
| 4,032,555 | 6/1977 | Bottaccio et al. . |
| 4,165,102 | 8/1979 | Bodmer . |
| 4,173,684 | 11/1979 | Stolfo . |
| 4,226,962 | 10/1980 | Stolfo . |
| 4,379,897 | 4/1983 | Asano et al. . |
| 4,447,952 | 5/1984 | Elkins . |
| 4,612,254 | 9/1986 | Ginter et al. . |
| 4,620,874 | 11/1986 | Booth, Jr. et al. . |
| 4,647,952 | 3/1987 | Pokora et al. . |
| 4,806,521 | 2/1989 | Umeda et al. . |
| 4,859,561 | 8/1989 | Metz et al. . |
| 4,920,091 | 4/1990 | Iwakura et al. . |
| 4,950,781 | 8/1990 | Nakanishi et al. . |

FOREIGN PATENT DOCUMENTS

| | | |
|---|---|---|
| 2025940 | 1/1980 | United Kingdom . |
| WO8900506 | 1/1989 | WIPO . |

OTHER PUBLICATIONS

"Curing of Novalak Phenol–Formaldehyde Resin w/Pyromellitic Dianhydride" Nikolaev et al. (USSR) Plast. Massey, (a), 66–7 (1989) (Abstract).

Primary Examiner—Cecilia J. Tsang
Assistant Examiner—Patrick R. Delaney
Attorney, Agent, or Firm—Thompson Hine & Flory LLP

[57] ABSTRACT

A carboxyl-containing phenolic resin represented by the formula:

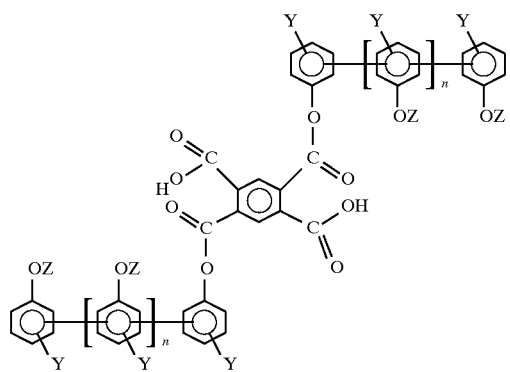

where n is 0 to 100, the phenolic units of the resin being directly bonded to one another through positions ortho or para to the OZ group; Z is selected from the group consisting of H and the residue of a mono or dianhydride, said mono or dianhydride having been reacted with a hydroxy group of a phenolic resin; and Y is present at a position meta or para to the OZ group and is selected from the group consisting of an alkyl group, a halogen atom, an aryl group, a phenylalkyl group, an alkyl group, a carboxyl group of the formula—COOR where R is H, an alkyl group or a phenylalkyl group, an alkoxy group, an aryloxy group, and an amino group of the formula—$NR_1R_2$ where $R_1$ and $R_2$ are the same or different and represent H or an alkyl group.

7 Claims, No Drawings

CARBOXYL-CONTAINING PHENOLIC RESIN DEVELOPER AND METHOD OF PREPARATION

BACKGROUND OF THE INVENTION

The present invention relates to novel phenolic developer resins having carboxyl functions incorporated onto the backbone of such resins and to a process for preparing such carboxyl-containing phenolic resins. More particularly, the invention relates to novel metal-modified carboxyl-containing phenolic resins for use as suitable carbonless dye developers.

Developer resins which produce colored images from colorless or substantially colorless materials are well-known. The preferred developer materials are principally phenol derivatives and phenolic resins. Phenols, biphenols, methylene bis-diphenols, phenol-formaldehyde novolak resins, metal processed novolak resins, salicylic acid derivatives and salts are representative examples of the phenolic developers that have been used. Such resins are described in more detail in U.S. Pat. Nos. 3,244,549 to Farnham 3,244,550 to Farnham; 3,672,935 to Miller; 3,934,070 to Kinura; 4,165,102 to Bodimer; 4,173,684 to Stolfo; 4,379,897 to Asano; and 4,612,254 to Ginter.

Among the color developers, phenol-formaldehyde condensates have been widely used because they exhibit excellent color development, good coating properties (rheology) and good water resistance. While phenol-formaldehyde condensates are advantageous color developers, certain questions have arisen regarding their use in recording materials. Because such resins are prepared from formaldehyde, there is concern that they may be unsafe from both the standpoint of their manufacture and their use in recording materials. Accordingly, much research has been directed to developing new and improved developer materials which are free of formaldehyde. For example, U.S. 4,647,952 to Pokora teaches the production of novel formaldehyde-free, phenolic resins for use as color developers in recording materials.

SUMMARY OF THE INVENTION

In accordance with the present invention, a novel phenolic resin developer containing one or more carboxyl functions is provided having improved developer characteristics by incorporating a carboxyl-containing compound such as a mono-or dianhydride, preferably a dianhydride such as pyromelletic dianhydride, onto the backbone of a phenolic resin. The starting resins of the present invention are phenolics such as novolac or resol resins and are, preferably, those prepared by the enzymatic oxidation coupling of a phenol such as the free radical addition polymerization of a phenol using the peroxide-peroxidase enzyme system described in commonly assigned U.S. Pat. No. 4,447,952, the contents of which is incorporated herein by reference.

The resulting carboxylated phenolic resin is effective in developing leuco dyes which otherwise do not provide strong colors with typical phenolic developers. These novel carboxyl-containing resins are particularly effective in developing acid sensitive yellow dyes, something the starting resins lack the ability to do.

The carboxylated phenolic resin developer can be subsequently metallated to further modify the developer. Preferably, the developer is reacted with a salt of a metal such as zinc, copper, cadmium, aluminum, indium, tin, chromium, cobalt, nickel and the like, and most preferably the metal is a zinc compound such as zinc chloride. In the case of zinc chloride, the resin can be zincated using standard techniques such as dissolving the resin in aqueous sodium hydroxide and adding zinc chloride. Alternatively, the developer can be zincated by adding the proper amount of zinc chloride before acidifying the reaction mixture. In either case, zincation of the developer gives it the ability to develop zinc sensitive cyan dye as well as other carbonless dyes such as CVL.

A principal object of the present invention is to provide a novel, carboxylated, formaldehyde-free, phenolic resin for use as a color developer in recording materials.

This and other objects are achieved in accordance with the present invention which, in one embodiment, provides:

A carboxyl-containing phenolic resin represented by the formula (I):

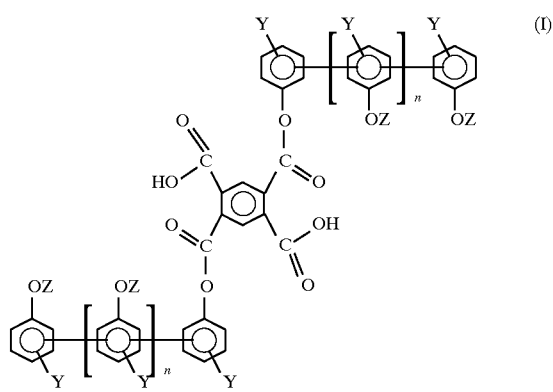

where n is 0 to 100, the phenolic units of the resin being directly bonded to one another through positions ortho or para to the OZ group; Z is selected from the group consisting of H and the residue of a mono or dianhydride, said mono or dianhydride having been reacted with a hydroxy group of a phenolic resin; and Y is present at a position meta or para to the OZ group and is selected from the group consisting of an alkyl group, a halogen atom, an aryl group, a phenylalkyl group, an alkyl group, a carboxyl group of the formula -COOR where R is H, an alkyl group or a phenylalkyl group, an alkoxy group, an aryloxy group, and an amino group of the formula -$NR_1R_2$ where $R_1$ and $R_2$ are the same or different and represent H or an alkyl group.

Another embodiment of the present invention relates to the carboxyl-containing phenolic resin developer wherein said carboxyl-containing phenolic developer resin is metallated, preferably with zinc.

Still another embodiment of the present invention relates to a process for preparing a carboxyl-containing, phenolic resin developer which comprises reacting a mono- or dianhydride with a phenolic resin where the phenolic resin is represented by the formula (II):

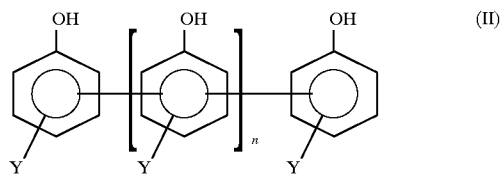

where n is 0 to 100, the phenolic units of the resin being directly bonded to one another through positions ortho and/or para to the hydroxy group and is selected from the group consisting of an alkyl group, a halogen atom, an aryl group, a phenylalkyl group, an allyl group, a carboxyl group of the formula - COOR where R is a hydrogen atom, an alkyl group or a phenylalkyl group, an amino group of formula—

$NR_1 R_2$ where $R_1$ and $R_2$ are the same or different and represent a hydrogen atom or an alkyl group.

In accordance with a more preferred embodiment of the invention, the phenolic resin is represented by the formula (III):

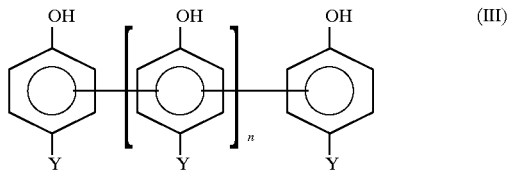

(III)

DETAILED DESCRIPTION OF THE INVENTION

Previous methods of producing a carboxylated phenolic resin developer for leuco dyes was to react a salicylic acid derivative with phenol and formaldehyde. Such a method is described in commonly assigned U.S. Pat. No. 4,226,962 to Stolfo. Generally, such methods are encumbered with the disadvantage of having to remove excess phenol from the polymerization reaction, usually by distillation which, in addition to being an extra step in the process, is an expensive time-consuming and difficult procedure. Furthermore, it is common for the phenol to preferentially react with the formaldehyde rather than the salicylic acid making it difficult to control the amount of salicylic acid units incorporated into the resin.

In accordance with the present invention, a carboxyl-containing phenolic resin is obtained by reacting a phenolic resin, preferably, a phenolic resin prepared by the enzymatic oxidative coupling of a phenol as described in commonly assigned U.S. Pat. Nos. 4,647,952 to Pokora, et al. and 4,900,671 to Pokora, et al., with a mono- or dianhydride such that carboxyl-containing groups are strategically incorporated along the backbone of the phenolic polymer chain.

Similarly, carboxylic groups may be incorporated on to the backbone of a phenolic resin by reacting the phenolic resin with an alkali metal hydroxide to deprotonate the hydroxyl and then reacting the reaction product with carbon dioxide followed by acidification. The reaction of an alkali metal salt of a phenol monomer with carbon dioxide to form o-hydroxylbenzoic acid is known and is generally referred to as the Kolbe reaction.

The phenolic resins useful in the process of the present invention are preferably those phenolic resins prepared by enzymatic oxidative coupling of phenols represented by the formula (I), and most preferably by formula (II) above.

The phenolic resins of this invention can be homopolymers or copolymers, i.e., the Y group in a given phenolic resin may be the same or different.

The resins are often mixtures of dimers, trimers, and higher molecular weight oligomers. Usually, the major part of the resin, i.e., greater than about 50% by weight of the resin, is trimer or higher molecular weight compounds. Preferably the resins useful in this invention are para substituted and have a molecular weight of up to about 3000 and most preferably from about 500 to 1,000.

The alkyl groups represented by Y in formulae (I) and (II) may contain up to about 10 carbon atoms and include such alkyl groups as t-butyl, n-butyl, octyl, nonyl, etc.

Where R, $R^1$ and $R^2$ represent alkyl groups, they are typically a lower alkyl group having 1 to 4 carbon atoms, such as methyl, ethyl, propyl, isopropyl, n-buty, sec-butyl and t-butyl.

Where Y is an aryl group, it is typically a phenyl group or substituted phenyl group such as halogen-substituted phenyl, an alkyl-substituted phenyl or a phenol group such as a 4'-phenol group.

Examples of a halogen atom include fluorine, chlorine, bromine and iodine.

Representative examples of phenylalkyl groups include benzyl, isopropylidene phenyl, butylidene phenyl, isopropylidene-4' phenol, and butylidene-4' phenol.

A particular advantage of the carboxyl-containing phenolic resin developers of this invention is their enhanced ability to develop strong colors from leuco dyes, particularly, acid sensitive yellow dyes. The non-carboxylated phenolic resins lack this ability.

The reaction scheme for the preparation of the carboxyl-containing phenolic resins of the present invention can be illustrated as follows:

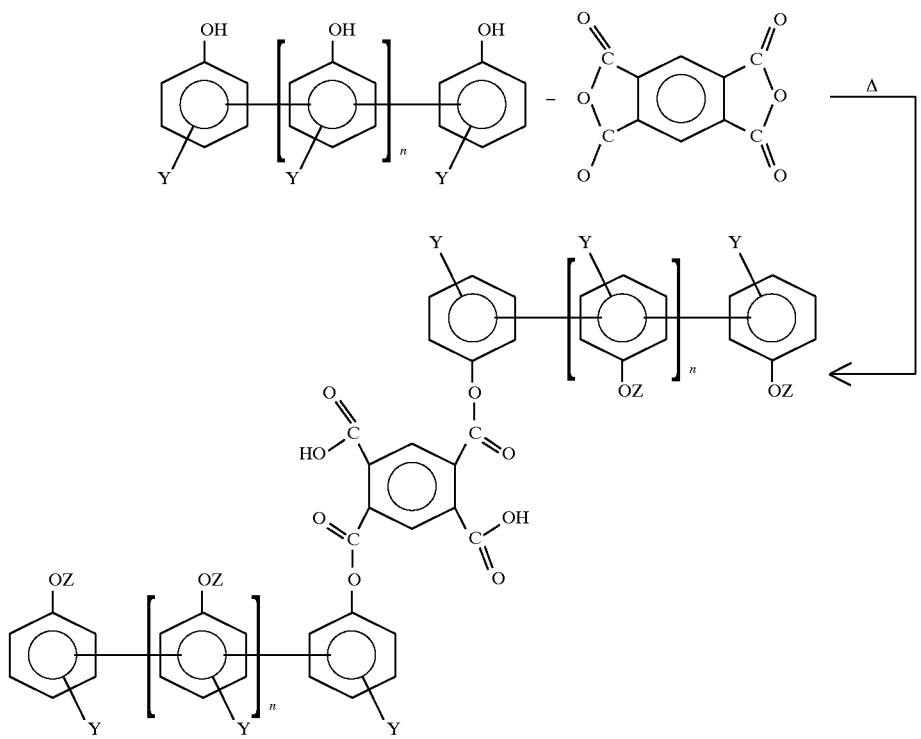

where n, y and z are identified as in formula (I).

The carboxyl-containing phenolic resin produced in the above-illustrated reaction contains at least one free carboxyl group resulting from the reaction and additional carboxyl groups may be generated by hydrolysis of any remaining anhydride functions.

While the reaction is particularly favorable for dianhydrides, mono anhydrides such as phthalic anhydride may also be employed. The mono anhydride, of course, will provide only a single carboxyl group resulting from the reaction.

As stated earlier, the carboxyl-containing phenolic resin developers of the present invention may be metal-modified in a manner analogous to known novolak developer resins to further improve their reaction with color precursors, particularly cyan dyes, and thereby improve the density and fastness of the image.

In addition to the metal modification methods described above, the resin may be melted and mixed with an alkanoate salt such as zinc propionate, zinc acetate or zinc formate in the presence of an ammonium compound such as ammonium carbonate or ammonium acetate. The practice described in U.S. Pat. No. 4,173,684 can also be used.

The zinc-modified phenolic developer resins can also be formed by reacting zinc oxide or zinc carbonate and ammonium benzoate or ammonium formate with the resins in a manner analogous to the teachings in U.S. Pat. Nos. 4,165,102 and 4,165,103.

The metal content of the metal-modified phenolic developer resins should be more than 0.5 percent by weight and may range up to 15 percent by weight. Usually, a range of about 1.5 to 5 percent by weight is used.

Recording materials employing the carboxyl-containing phenolic resin developers of the present invention can be prepared in a conventional manner. To provide a developer sheet, the carboxyl-containing phenolic developer resin may be dissolved in an appropriate solvent (typically acetone) and applied to the surface of the paper by blade or roll coating or the like. Alternatively, the developer resin may be used in the form of a resin grind analogous to the resin grinds described in U.S. Pat. No. 3,924,027 to Saito et al. For example, the resin may be pulverized and mixed with an organic high molecular compound such as starch or styrene-butadiene latex. This mixture is dispersed in water or a solvent that does not readily dissolve the phenolic developer resin or the high molecular compound and coated on an appropriate support.

The developer resin is usually applied in an amount of about 0.2 to 0.4 lbs. of resin/1300 sq. ft. (solids).

Where a self-contained recording material is desired, a mixture of the phenolic developer resin and microcapsules containing the dye, can be coated upon a support as one layer or the developer and the microcapsules, can be applied in separate layers. For the preparation of photosensitive recording materials, see U.S. Pat. Nos. 4,399,209 and 4,440,846 which are incorporated herein by reference.

The invention is illustrated in more detail by the following non-limiting example.

EXAMPLE 100 grams of a phenolic resin prepared by the enzymatic oxidative coupling of p-t-butylphenol are ground with 8 grams of pyromelletic dianhydride and heated to a temperature of 150° C. to provide a carboxyl-containing phenolic resin.

The carboxyl-containing phenolic resin is dissolved in an aqueous sodium hydroxide solution and 10 grams of zinc chloride are added to the solution to form the zincated carboxyl-containing phenolic resin as a white precipitate. The resulting zincated resin exhibits the ability to develop zinc sensitive cyan dye.

Having described the invention in detail and by reference to preferred embodiments thereof, it will be apparent that modifications and variations are possible without departing from the scope of the invention defined in the appended claims.

What is claimed is:

1. A phenolic developer resin having free carboxyl groups represented by the formula:

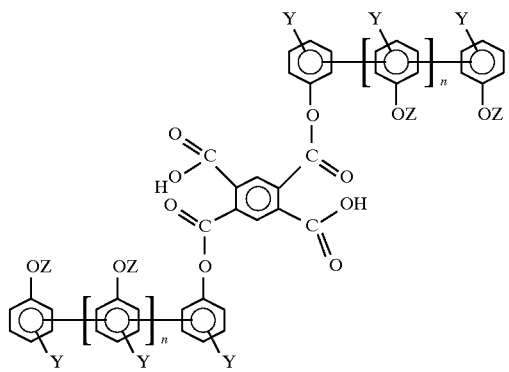

where n is 0 to 100, the phenolic units of the resin being directly bonded to one another through positions ortho or para to the OZ group; Z is selected from the group consisting of H and an ester linkage with a pyromellitic dianhydride moiety; and Y is present at a position meta or para to the OZ group and is selected from the group consisting of a halogen atom, an aryl group, a phenylalkyl group, an alkyl group, a carboxyl group of the formula —COOR where R is H, an alkyl group or a phenylalkyl group, an alkoxy group, an aryloxy group, and an amino group of the formula —$NR_1R_2$ where $R_1$ and $R_2$ are the same or different and represent H or an alkyl group.

2. The carboxyl-containing phenolic developer resin of claim 1 wherein said resin is further reacted with a salt of a metal selected from the group consisting of zinc, copper, cadmium, aluminum, indium, tin, chromium, cobalt and nickel to yield 5 a metal-modified, carboxyl-containing, phenolic resin.

3. The carboxyl-containing phenolic developer resin of claim 2 wherein said metal is zinc.

4. A recording material comprising a phenolic developer resin having free carboxyl groups represented by the formula:

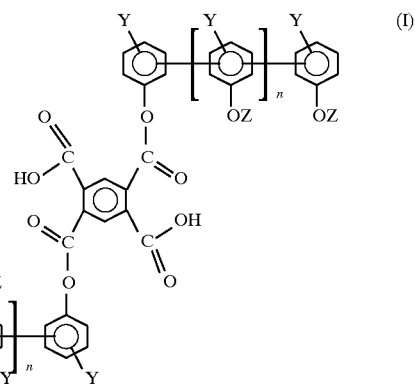

where n is 0 to 100, the phenolic units of the resin being directly bonded to one another through positions ortho or para to the OZ group; Z is selected from the group consisting of H and an ester linkage with a pyromellitic dianhydride moiety; and Y is present at a position meta or para to the OZ group and is selected from the group consisting of an alkyl group, a halogen atom, an aryl group, a phenylalkyl group, a carboxyl group of the formula - COOR where R is H, an alkyl group or a phenylalkyl group, an alkoxy group, an aryloxy group, and an amino group of the formula -$NR_1R_2$ where $R_1$ and $R_2$ are the same or different and represent H or an alkyl group.

5. The recording material of claim 4 wherein said phenolic developer resin is reacted with a salt of a metal selected from the group consisting of zinc, copper, cadmium, aluminum, indium, tin, chromium, cobalt and nickel to yield a metal-modified, phenolic developer resin.

6. The recording material of claim 5 wherein said metal is zinc.

7. The recording material of claim 4 further comprising an imaging sheet for forming images by image-wise reaction of one or more chromogenic materials with said phenolic developer resin, said imaging sheet comprising:
 (a) a substrate, and
 (b) a layer of microcapsules coated on one surface of said substrate, said microcapsules containing an internal phase:
 (i) a chromogenic material, and
 (ii) a radiation curable composition which undergoes a change in viscosity upon exposure to actinic radiation, wherein images are formed on said imaging sheet by exposing said imaging sheet to actinic radiation, rupturing said microcapsules in the image areas such that said internal phase is image-wise released from said ruptured microcapsules and transferred to said phenolic developer resin wherein a patterned image-forming reaction occurs between said chromogenic material and said phenolic developer resin.

* * * * *